United States Patent [19]

Handy et al.

[11] 4,075,885
[45] Feb. 28, 1978

[54] ROCK BOREHOLE SHEAR TESTER

[75] Inventors: Richard L. Handy, Des Moines; Leon E. Girard, Ames; Bruce R. Roorda, Marshalltown, all of Iowa; John M. Pitt, Woodridge, Va.

[73] Assignee: Iowa State University Research Foundation, Inc., Ames, Iowa

[21] Appl. No.: 771,360

[22] Filed: Feb. 23, 1977

[51] Int. Cl.² ............................................. E21B 49/00
[52] U.S. Cl. .................................................. 73/88 E
[58] Field of Search .......................... 73/101, 84, 88 E

[56] References Cited

U.S. PATENT DOCUMENTS 3,175,392  3/1965  Tharalson et al. ................ 73/101 X

FOREIGN PATENT DOCUMENTS 389,434   3/1973   U.S.S.R. ............................. 73/88 E
422,842  10/1973   U.S.S.R. ............................. 73/88 E

Primary Examiner—Jerry W. Myracle
Attorney, Agent, or Firm—Zarley, McKee, Thomte, Voorhees & Sease

[57] ABSTRACT

An expansible shear head device within a pulling cradle is lowered into a bore hole; and the device is expanded hydraulically to exert a predetermined normal pressure on the side walls of the bore hole. The pressure plates of the device are ribbed for permitting interlocking with the rock. Vertical shear stress is exerted on the rock by pulling on the device. The shear head includes a body having a plurality of hinge points, and is laterally expansible. A laterally extendible plunger with a movable shear plate is mounted opposite to a similar shear plate which is secured to permit some deflection of the body about its hinge points from its normal parallel configuration as the shear force moves the body through the bore. The body is locked in its normal parallel configuration until the shear force is applied.

16 Claims, 5 Drawing Figures

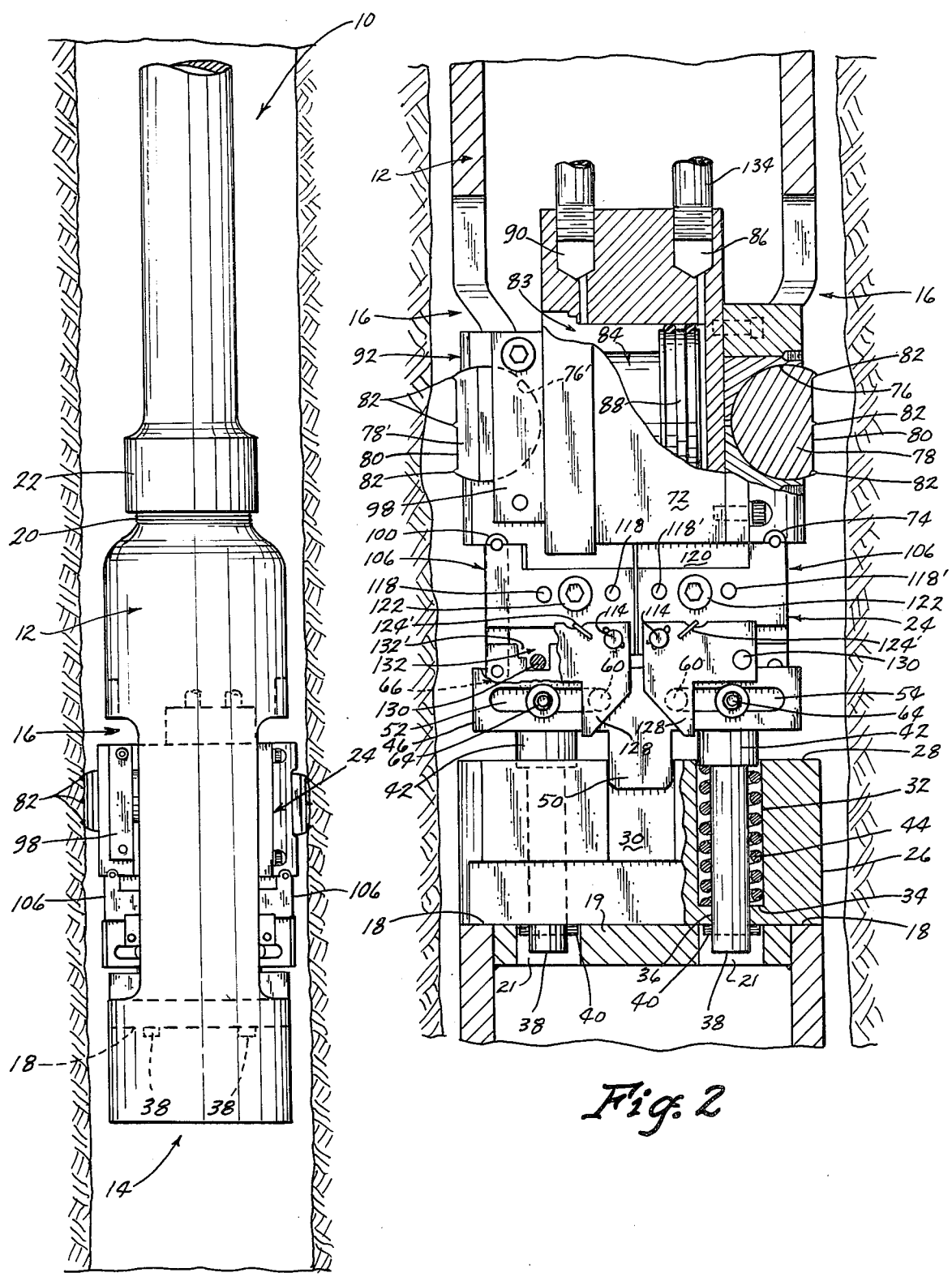

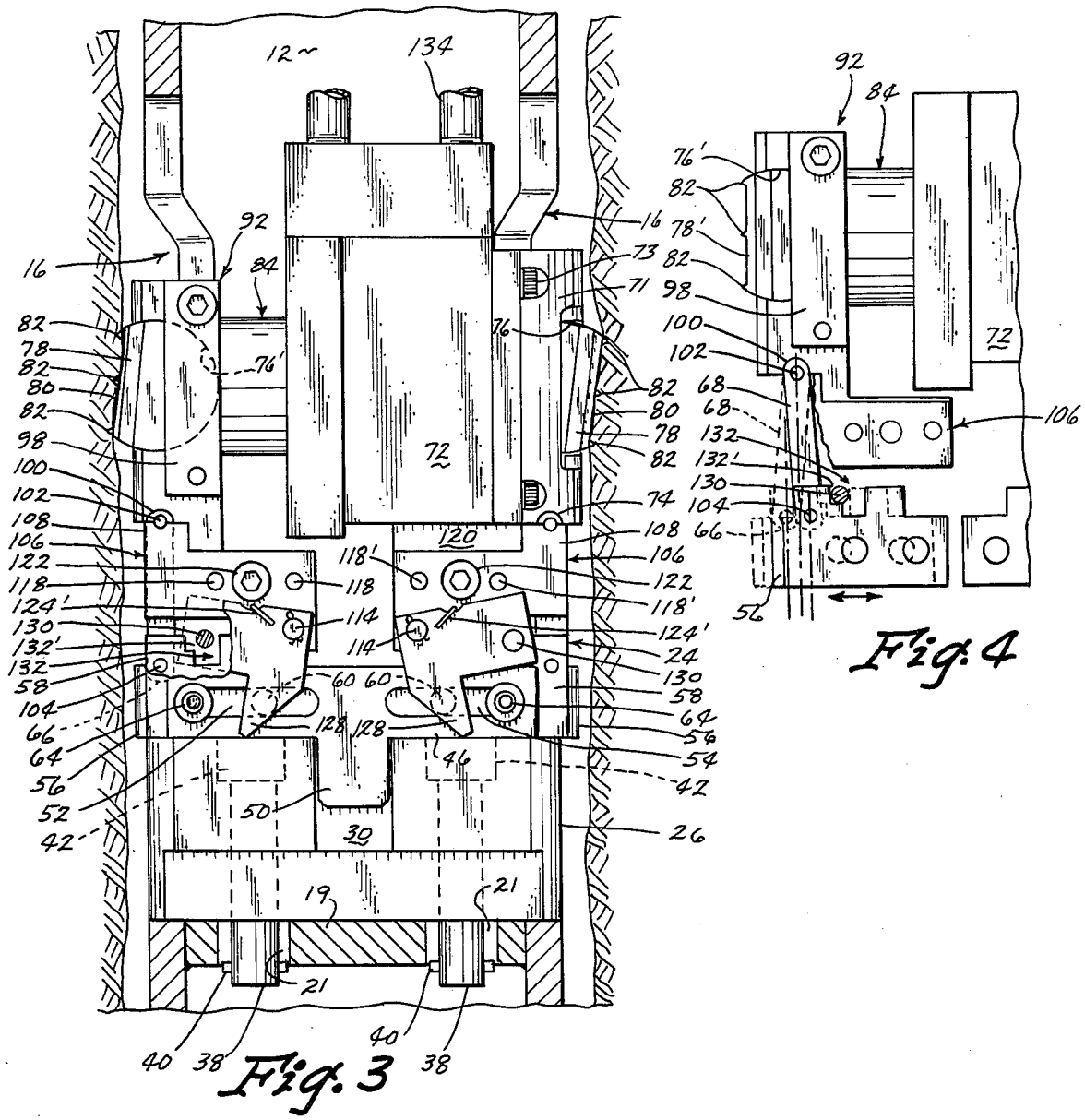

ROCK BOREHOLE SHEAR TESTER

BACKGROUND OF THE INVENTION

This invention is related to the subject matter of U.S. Pat. Nos. 3,427,871, and 3,673,861 issued Feb. 18, 1969 and July 4, 1972, respectively, which describe methods and apparatus for testing soil. The present invention pertains to improvements over these prior devices and methods. More specifically, this invention relates to a rock borehole shear tester.

Tester of the prior art have used laterally expandable shear plates. However, the shear plates were incapable of lateral movement as shear forces were applied to accommodate irregularities in the bore. Further, prior shear heads could not accommodate changes in soil volume during shear (i.e., "dilatancy"). The shear head of this invention can permit limited movement of the expandable shear plates during shear. The pivot points in the head allow it to expand or contact slightly as the rock changes in volume during shear.

The shear plates on the device of this invention are mounted upon expandable equalizer plates which are held parallel during initial expansion to allow use in variable size holes without introducing force. The lock is released upon application of the shearing stress, and resets automatically at the conclusion of a test.

The shear plates are rotatable inserts, for easier replacement and to better conform to roughness in the hole. The shear plates are preferably pushed, rather than pulled, and this is accomplished by mounting the shear head in the bottom of the pulley cradle which is pulled upwardly by conventional apparatus. Only one test may be conducted at each contact, but as many as four tests may be performed at the same depth by rotating the shear head and pulling cradle. Uniform pressure is exerted on the shear head by a pressure block that engages the expanded shear head after the pressure plates have engaged the rock, and after the shear force has been applied.

BRIEF DESCRIPTION OF THE DRAWINGS

This invention consists in the construction, arrangement and combination of the various parts of the device and in the sequence of steps of the method, whereby the objects contemplated are attained as hereinafter more fully set forth, specifically pointed out in the claims, and illustrated in the accompanying drawings, in which:

FIG. 1 is an elevational view of the device of this invention as positioned in a rock borehole which is shown in section;

FIG. 2 is an enlarged scale partial sectional view of the shear head and pulley cradle before lateral expansion of the unit has taken place;

FIG. 3 is a view similar to FIG. 2 but shows the shear plates in contact with the rock and shows the pressure block applying upward vertical shearing force to the shear head;

FIG. 4 shows the non-parallel position of an equalizer plate after it has become unlocked as a shearing force is applied.

DESCRIPTION

Figure 5:
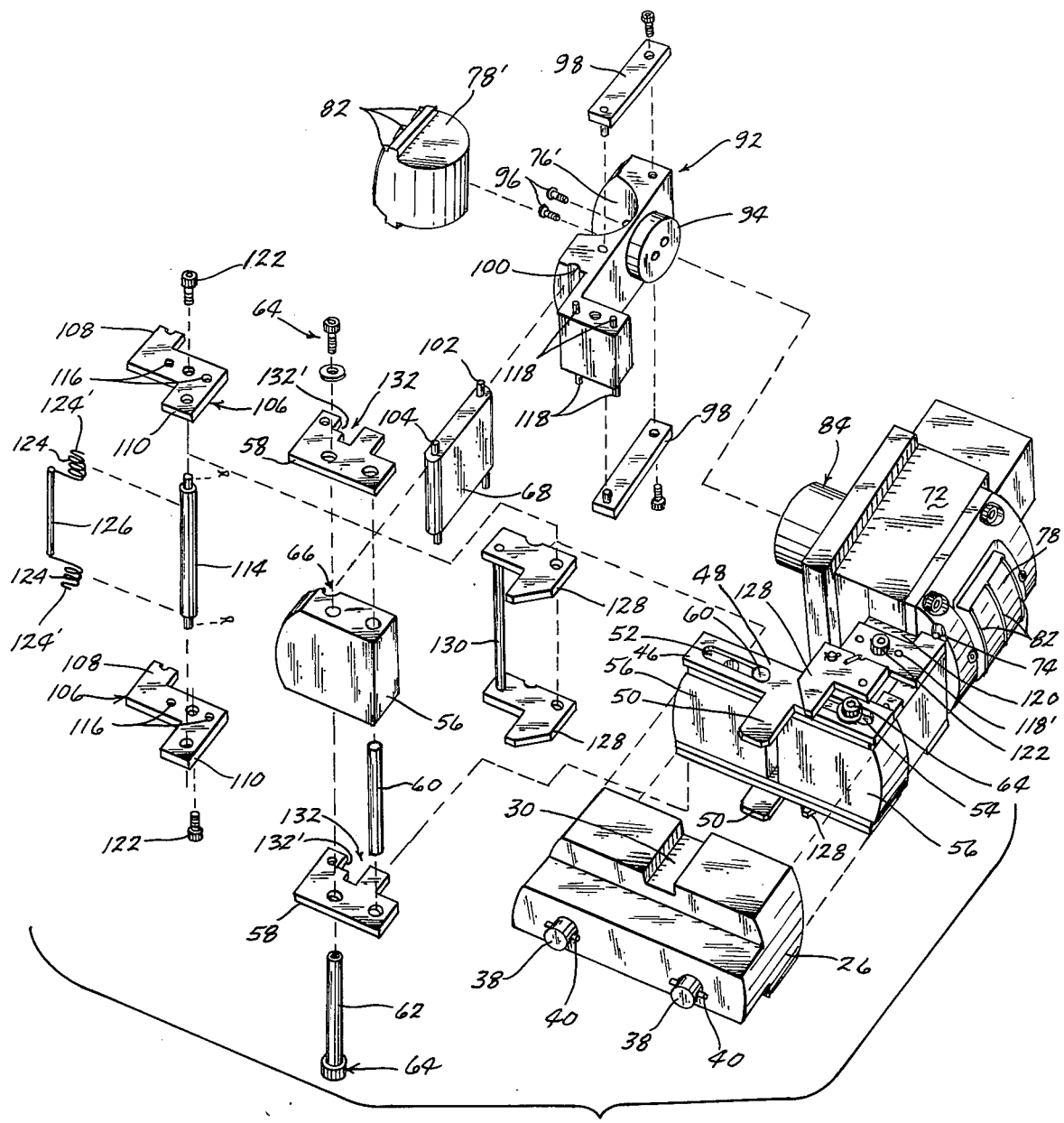
FIG. 5 is a perspective view of the shear head with some of its component parts being shown in exploded fashion.

The numeral 10 designates a rock bore hole in the order of 3 inches in diameter. Pulling cradle 12 is a hollow cylinder with an open bottom 14, opposite side slots 16 having bottom edges 18, and a threaded top portion 20 (FIG. 1). A suitable coupling and pipe 22 are secured to the upper end of cradle 12 to effect both its positioning in the bore as well as to effect the exertion of shearing forces (vertical movement) on the cradle. The specific apparatus for effecting the shearing force has not been shown. Plate 19 with holes 21 is welded to cradle 12 at the bottom edges 18 of slots 16.

A shear head 24 is mounted in cradle 12 and is positioned between the slots 16. A horizontal pressure plate 26 rests on plate 19. Plate 26 has a flat upper surface 28. Two vertical guide slots 30 appear on opposite sides thereof. Two vertical bores 32 extend downwardly therein and terminate in bottoms 34. Smaller bores 36 extend through the bottoms 34 and slidably receive pins 38. Keys 40 limit the upward movement of pins 38 through the bores 36. The upper ends of pins 38 terminate in heads 42 which slidably engage the walls of bores 32. Springs 44 normally yieldably maintain the heads 42 slightly above the level of the upper surface of block 26 as shown in FIG. 2. The lower ends of pins 38 can extend into holes 21 of plate 19.

Two T-shaped stop plates 46 have a horizontal flange 48 and a central flange 50 which extends in a downwardly direction to be slidably received in one of the guide slots 30 of block 26. Each flange 48 has two horizontal slots 52 and 54 therein. Foot members 45 are slidably mounted between plates 46 as are pairs of link retainers 58. Pins 60 extend through aligned apertures in each foot member 56 and the opposite two retainers 58. The opposite ends of pins 60 are adapted to nest in the inner ends of slots 52 to limit the sliding travel of the members 56 towards each other. Pins 62 similarly extend through aligned apertures in each foot member 56 and the opposite two retainers 58 and are adapted to nest in the outer ends of slots 52 to limit the sliding movement of said members 56 away from each other. Keepers 64 on opposite ends of pins 62 maintain the assembly of these components.

Each foot member 56 has an arcuate groove 66 in its outer upper surface. Identical shear plate links 68 and 70 have their rounded lower ends rotatably nested in grooves 66.

A cylinder shear plate adapter 71 attached by screws 73 to blodk 72 has an arcuate grooe 74 (FIGS. 2, 3 and 4) to receive the rounded upper end of link 70. One face of adapter 71 has a horizontally disposed groove 76 (of more than 180° in circumference, see FIG. 2) to rotatably receive shear plate 78 which is of complimentary shape. The outer face 80 of plate 78 is cylindrically shaped with three horizontal sharpened and spaced apart ribs 82 projecting outwardly therefrom. Block 72 includes a horizntal bore 83 into which piston 84 is mounted. Hydraulic fluid entering bore 83 through port 86 above piston head 88 causes the piston to move outwardly. Hydraulic fluid entering bore 83 through port 90 below head 88 causes the piston to move inwardly.

An L-shaped push plate 92 has a round lug 94 adapted to be secured to the outer end of piston 84 by screws 96. Plate 92 has a groove 76' identical to groove 76 adapted to receive a shear plate 78' identical to plate 78. Upper link retainers 98 are secured in any convenient way to the opposite sides of plate 92 to maintain plate 78' within groove 76'. An arcuate groove 100 (FIGS. 2, 3 and 5) in plate 92 receives the rounded upper end of link 68.

Links 68 and 70 have pins 102 and 104 extending through their respective upper and lower ends. Links 106 have oppositely disposed flanges 108 and 110, with flange 108 having an arcuate notch 112 therein. Notches 112 embrace the outer ends of the upper pins 102 in links 68 and 70. Pairs of links 106 are coupled together by pin 114 (FIG. 5) which extends through apertures in the lower flange 110. As seen in FIG. 5, the left-hand pair of links 106 have apertures 116 which fit on pins 118 on the lower end of equalizer plate 92. Screws 122 secure links 106 to the plate 92. The right-hand pair of links 106 (assembled portion of FIG. 5) similarly apertures which fit on pins 118' which extend from block extensions 120 of cylinder block 72. A screw 122 holds these links 106 in place. As also seen in FIG. 5, torsion springs 124 are secured to and around the ends of pins 114 and are interconneced by bars 126. The ends 124' of springs 124 extend upwardly and over L-shaped extension links 128 which are also mounted on the ends of pins 114 (See FIGS. 2 and 3). Pairs of extension links 128 are secured together by rod 130. Springs 124 bias to links 128 in the normal position shown in FIG. 2. In this position, rod 130 lays on the top edge of stop plates 46 and passes through and engages the bottom of notch 132 in links 58. The bar 126 engages the underside of links 106. This represents the locked position for shear plate links 68 and 70, since they are held substantially rigid and parallel, and the pivotal connections at the upper and lower ends thereof are not operative.

DESCRIPTION OF THE PREFERRED EMBODIMENT

The pulling cradle 12 is lowered into the bore 10 to the desired depth. The components then appear as shown in FIG. 2. Hydraulic fluid is applied to line 134 connected to port 86 to cause plunger or piston 84 to expand. At this point in time, the upper porton of the shear head 24 is supported on the heads 42 of pins 38, which in turn are supported by compression springs 44. This frees the sliding foot members 56 from frictional engagement with the upper surface of block 26.

As the shear plate 78 engages the wall of the bore hole 10 through the slot 16, the cylinder block 72 moves in an opposite direction until the shear plate 78' engages the opposite wall of the bore hole 10 through the opposite slot 16.

This action of expanding the piston 84 and engaging the shear plates 78 and 78' with the rock continues until the ribs 82 penetrate the rock. The plates 78 and 78' can rotate about a horizontal axis to conform to any irregularities in the rock, as shown in FIG. 3. The foregoing operation causes the lower link assemblies to divide and move from the position of FIG. 2 to the position of FIG. 3. More specifically, the equalizer plate 92 carries with it the components below connected thereto; and the cylinder block 72 carries with it the similar components below that are interconnected therewith. Only the stop plates 46 remain stationary, and the slots 52 and 54 allow the outward movement of the separate upper assemblies.

This application of normal force is accomplished without any friction between the sliding assemblies and the upper surface of pressure 26, because the springs 44 and pins 48 maintain the upper portion of the shear head 24 out of engagement with plate 26. In addition, links 128 are in the above described locked position shown in FIG. 2. which maintains the pivotally mounted shear plate links 68 and 70 in a parallel rigid condition.

Pressure in a vertical direction can be applied in any desired manner to cradle 12, such as hydraulically from below, or by pulling the cradle upwardly in a slow manner according to conventional techniques. The upward movement of the cradle 12 also moves plate 26 upwardly. Springs 44 are compressed causing pins 38 to recess within the plate whereby the upper surface 28 of the plate moves into contact with the bottoms of foot members 56. Just before this contact is made, the plate 56 engages the lower tips of links 128 causing them to rotate upwardly and outwardly from the positions in FIG. 2 to the position of FIG. 3. It will be seen in FIG. 3 that the rod 130 has moved upwardly out of the bottom of notch 132, thus freeing the shear plate links 68 and 70 for limited pivotal movement. The secondary notch 132' in link retainers 58 serves to limit the movement of rod 130. The dotted lines in FIG. 4 illustrate the outward movement of link 68. The purpose of the pivotal movement given to these components after the vertical shearing force has been applied is to give the shear head 24 some limited flexibility to accommodate variations in the bore hole diameter as the upward movement of the unit takes place.

The measurements of the shear phenomenon through the application of the normal and shearing forces, as described above, are made through conventional procedures not unlike those enumerated in U.S. Pat. No. 3,427,871. Additional measurements could be made at the same elevations in the bore hole 10 by retracting the piston 84, lowering the device to the original level, rotating the device 45° or so, and repeating the foregoing operation.

The shear plate contact areas 80 conform to the circumference of the borehole 10. The three circumferential ridges or ribs 82 project outward and penetrate the rock, in order to effect a transfer of shearing stress into the rock itself, rather than between the rock and the plate surface. Although the ridges 82 thus are essential, their penetration also damages the rock, disrupting part of the measurable strength. To reduce this error in the determination of strength, the ridges are spaced apart as far as practicable. Experimentally it has been found that the spacings between ridges may be as much as 20 times the ridge base width with satisfactory results. In general, however, a shorter spacing is preferable to prevent eruption of the rock shear surface between the ridges, shortening the rock shear surface. Another upper limitation in spacing is the shearing strength of the ridge itself, which relates to the maximum measurable rock strength according to the formula $$\tau_{max} = R \times S/W$$

where $\tau_{max}$ is the maximum rock strength which can be measured before the wedges inducing the shear breaks off, and $R$ is the wedge shearing strength. Both $\tau_{max}$ and $R$ have dimensions of force per unit area, as pounds per square inch. The other two parameters in the formula, $W$ and $S$, respectively, represent the ridge base width and the spacing between corresponding points on successive ridges. Some representative solutions of this formula based on an allowable ridge shearing stress of 65,000 pounds per square inch, as for hardened tool steel, are shown in Table 1. t Table 1

Effects of Shear Plate Ridge Width and Spacing
on Maximum Measurable Rock Strength and the
Percent Loss of Cohesive Strength
due to Rock Damage

| $\frac{W}{D} = \frac{\text{Width}}{\text{Spacing}}$ | max, pounds per square inch* | D = Damage, Percent |
|---|---|---|
| 1/20 | 3,250 | 11 |
| 1/10 | 6,500 | 25 |
| 1/8 | 8,125 | 33 |
| 1/5 | 13,000 | 67 |

As previously mentioned, the minimum spacing between ribs 82 also is limited because of rock breakage in the vicinity of the ridges. Theoretical considerations and actual measurements indicate that for symetrial ridges with a 60° apical angle the extent of the damage relates to the ridge spacing by the following formula:

$$D = 100 \, (2W/S\text{-}2W)$$

where $D$ is the percent damage and $W$ and $S$ are ridge width and spacing, as before. Since the pieces of damaged rock remain in contact and still exhibit frictional resistance during the test, the damage factor D affects mainly the determinaton of rock cohesion and not its internal friction. Representative solutions of this equation are also shown in Table 1.

As can be seen in Table 1, the most useful range of ridge width-to-spacing ratio W/D is about 1/5 to 1/20, the actual selection of a ratio representing a trade-off between maximum measurable rock strength and an acceptable level of damage. A ratio of 1/10 was arbirarily selected for a standard, but other ratios in the range 1/5 to 1/20 also would perform satisfactorily. The application should cover the latter range in wedgte width:spacing ratio.

In viwew of the foregoing, it is seen that this invention will achieve at least all of its stated objectives.

What is claimed is:

1. A method of in situ determination of rock properties by forming a bore hole in the rock under test, introducing into said bore a device for determining the shear strength of rock at different measured applied normal stresses, including a hinged shear head having a plurlity of hinged points, and at least one of two oppositely mounted shear plates adaptable for lateral movement with respect to the axis of said bore, the invention comprising, moving said movable shear plate laterally until said shear plates engage and grip opposite surfaces of said bore,
   maintaining said hinged shear head in a substantially rigid configuration while said movable shear plate is being moved,
   exerting a shearing force on said body means in a direction parallel to the axis of said bore to exert a shearing force to the opposite surfaces of said bore through said shear plates, and simultaneously releasing said shear head from its rigid configuration to permit limited deformation thereof while said shearing force is being applied, and measuring the shearing resistance of the rock engaged by said shear plates.

2. The method of claim 1 wherein said shear plates are moved about an axis perpendicular to the axis of said bore to accommodate for variations in the surface of said bore engaged by said shear plates.

3. The method of claim 1 wherein said shearing force is applied through engaging said shear head with a pressure plate, but separating said pressure plate from said shear head while said movable shear plate is being moved.

4. A device for determining the shear strength of rock, comprising,
   a support means adapted to be suspended within a bore in the rock being tested,
   a shear head mounted on said support means, said shear head including a plurality of hinge points,
   at least one plunger mounted for lateral movement on said shear head,
   a first shear plate mounted on said plunger and being adapted to engage a first portion of the surface of said bore when said plunger is laterally extended,
   a second shear plate mounted on said body member opposite to said plunger and being adapted to engage a second portion of the surface of said bore when said plunger is extended.
   lock means on said shear head for releasably maintaining said shear head in a rigid configuration,
   means for exerting a shearing force on said shear head and to release said shear head from said rigid configuration to permit some deformation thereof through said hinge points as said shearing force is applied.

5. The device of claim 4 wherein said shear plates are pivotally mounted to accommodate for variations in the surface of said bore engaged by said shear plates.

6. The device of claim 4 wherein said support means includes a pressure plate element, said shear head being positioned adjacent said plate element, and control means limiting the engagement of said plate elements with said shear head while said plunger is being laterally moved, said control means permitting full and substantial engagement of said shear head and said plate element when shearing force is applied.

7. The device of claim 5 wherein said shear head has laterally expandable link assemblies in juxtaposition to said pressure plate, said link assemblies being operatively connected to move laterally in conjunction with the lateral movement of said plunger.

8. The device of claim 4 wherein said lock means comprising spring loaded pivotal links on said shear head, which engage a pressure plate when shearing force is applied thereto, said pressure plate comprising a part of said support means.

9. The device of claim 4 wherein said support means is a cylindrical cradle having access slots through which said pressure plates can laterally move.

10. The device of claim 7 wherein said shear head includes means to substantially center said expandable link assemblies with respect to said pressure plate.

11. The device of claim 4 wherein said shear head includes normally vertically disposed spaced apart parallel shear plate links when said shear head is in its rigid configuration.

12. The device of claim 4 wherein said shear plates are arcuately shaped to conform substantially to said borehole, and a plurality of spaced apart ribs are in said shear plates to penetrate the rock being tested.

13. A device for determining the shear strength of rock, comprising,
   a support means adapted to be suspended within a bore in the rock being tested,
   a shear head mounted on said support means, said shear head including a plurality of hinge points, at least one plunger mounted on lateral movement on said shear head, a first shear plate mounted on said plunger and being adapted to engage a first portion of the surface of said bore when said plunger is laterally extended, a second shear plate mounted on said body member opposite to said plunger and being adapted to engage a second portion of the surface of said bore when said plunger is extended, said shear plates being pivotally mounted to accommodate for variations in the surface of said bore engaged by said shear plates, and means for exerting a shearing force on said shear head.

14. The device of claim 13 wherein said shear plates are arcuately shaped to conform substantially to a borehole, and a plurality of spaced apart ribs are on said shear plates to penetrate the rock being tested.

15. The device of claim 14 wherein said ribs are extended from a base width to a sharpened edge, and the ratio between the base width of the ribs and the spacing between ribs is between 1/5 and 1/20.

16. The device of claim 15 wherein the ratio between the base width of the ribs and the spacing between ribs is 1/10.

* * * * *